United States Patent [19]

Nelson et al.

[11] Patent Number: 5,369,010

[45] Date of Patent: Nov. 29, 1994

[54] MONOCLONAL ANTIBODY TO POLYMORPHIC HLA DETERMINANT -B27

[75] Inventors: Karen A. Nelson, Seattle; Douglas M. Strong, Edmonds, both of Wash.

[73] Assignee: Genetic Systems Corporation, Seattle, Wash.

[21] Appl. No.: 14,063

[22] Filed: Feb. 5, 1993

Related U.S. Application Data

[63] Continuation of Ser. No. 601,597, Oct. 18, 1990, abandoned, which is a continuation of Ser. No. 449,490, Dec. 11, 1989, abandoned, which is a continuation of Ser. No. 766,739, Aug. 16, 1985, abandoned.

[51] Int. Cl.$^5$ .............. C07K 15/28; C12N 5/20; G01N 33/577
[52] U.S. Cl. .............. 435/7.24; 435/7.9; 435/172.2; 435/240.27; 435/975; 436/548; 436/821; 530/388.7; 530/388.73; 530/391.3
[58] Field of Search ............ 435/7.24, 7.9, 172.2, 435/240.27, 975; 436/548, 821; 530/388.7, 388.73, 391.3

[56] References Cited

U.S. PATENT DOCUMENTS

| | | | |
|---|---|---|---|
| 4,471,056 | 9/1984 | Grumet et al. | 436/548 |
| 4,517,289 | 5/1985 | Milford et al. | 436/548 |
| 4,623,621 | 11/1986 | Pestka | 436/548 |
| 4,628,027 | 12/1986 | Gay | 436/540 |
| 4,816,567 | 3/1989 | Cabilly et al. | 530/387 |

FOREIGN PATENT DOCUMENTS

| | | |
|---|---|---|
| 6578286 | 6/1987 | Australia . |
| 0204522 | 12/1986 | European Pat. Off. . |
| 8304102 | 11/1983 | WIPO . |
| 8403106 | 8/1984 | WIPO . |

OTHER PUBLICATIONS

Breur and Ivanyi, *Histocompatibility Testing 1984*, Eds. E. D. Albert et al., Springer-Verlag Press, Berlin, 1984, p. 144, describe qualities of four anti-B27 monospecific typing sera across four human races.

de Waal et al., *Histocompatibility Testing 1984*, eds. E. D. Albert et al., Springer-Verlag Press, Berlin, 1984, p. 418.

Grumet et al., *Hum. Immunol.* (1982) 5:61, describe a monoclonal antibody (B27M2) which divides HLA-B27 into two subgroups, and also recognizes B47.

Trapani, Joseph A. et al., *Hum. Immunol.* (1983) 7:205, Description of a Mouse Monoclonal Anti-HLA-B27 Antibody HLA-ABC-m3.

Antonelli, Paolo et al., Recognition of a unique HLA-B27,7,w22,17,14,w63,w46-Common Epitope by Two Independently Derived Balb/c-Monoclonal Antibodies. *Human Immunology* 8:296-297 (1983).

Breuning, M. H. et al., Subtypes of HLA -B27 Detected by Cytotoxic T Lymphocytes and Their Role in Self-Recognition. *Human Immunology* 5:259-268 (1982).

Ellis, Shirley A. et al., Recognition of HLA-B27 and Related Antigen by a Monoclonal Antibody. *Human Immunology* 5:49-59 (1982).

Rebai, Najet et al., Murine H-2D$^d$-Reactive Monoclonal Antibodies Recognize Shared Antigenic Determinant(s) on Human HLA-B27 or HLA-B27 Molecules or Both. *Immunogenetics* 17:357-370 (1983).

Yang et al., *Chem. Ab.* 98:213806, (1983).

Johnson et al., 11th Ann. Meeting Am. Soc. Histocompatibility & Immunogenetics, *Hum. Immunol.* 14:134-135 (1985).

Weiss et al., *Chem. Ab.* 104:143088 (1986).

Ellis et al, Human Immunology, vol. 5, 1982 pp. 49-59.

*Primary Examiner*—David Saunders
*Attorney, Agent, or Firm*—Townsend and Townsend Khourie and Crew

[57] ABSTRACT

Novel cell lines, receptors and monoclonal antibodies prepared therefrom that are specific for the human HLA-B27 antigen are provided. The monoclonal antibodies are useful in diagnosis and therapy, particularly with respect to certain rheumatoid disorders.

18 Claims, No Drawings

MONOCLONAL ANTIBODY TO POLYMORPHIC HLA DETERMINANT -B27

REFERENCE TO RELATED APPLICATIONS

This application is a continuation of Ser. No. 07/601,597, filed Oct. 18, 1990 and now abandoned, which is a continuation of Ser. No. 7/449,490, filed Dec. 11, 1989 and now abandoned, which is a continuation of Ser. No. 06/766,739. filed Aug. 16, 1985 and now abandoned.

FIELD OF THE INVENTION

The present invention relates to the development of cell lines capable of secreting receptors specifically reactive with the HLA-B27 antigen and, more particularly, to the production of monoclonal antibodies that recognize the human HLA-B27 antigen, but which exhibit minimal cross-reactivity to other human HLA antigens.

BACKGROUND OF THE INVENTION

The HLA (human leukocyte antigens), or so-called "histocompatibility antigens", are glycoprotein molecules found on the surface of all nucleated somatic cells, as well as all white blood cells in the human body. The HLA antigens are encoded by four loci on human chromosome six. There is a high degree of polymorphism at each locus. Initially, these antigens were used primarily in donor-recipient matching for organ transplantation. Some of these antigens have since been shown also to be associated with susceptibility to various diseases.

In particular, rheumatic disorders are believed to be closely associated with the HLA system. Notably, a number of diseases characterized by sacroilitis and with seronegative peripheral arthritis have a reported distinct association with one antigen, the HLA-B27 antigen. For individuals whose cells express B27 antigen, the relative risk for manifesting one of these diseases is 30 to 200 times that of an individual without the B27 antigen. Also, the relative risk of contracting Ankylosing Spondylitis is about 200 times greater in B27-positive than in B27-negative individuals.

Presently, the HLA system is defined by reactions of alloantisera with human leukocytes. These reactions have been interpreted as defining multiple specificities for the products of each locus. There are 47 known specificities for HLA-B antigen, one being HLA-B27. In addition, HLA antigens vary in their distribution among racial groups. Thus, an individual's race must be considered when assigning HLA phenotypes.

Generally, serologic testing for HLA antigen requires extreme caution with respect to the cross-reactivity of the antigens with the reagent sera. This is due to the fact that most antisera utilized for determining the presence of a particular antigen often cross-react with other antigens, and/or contain antibodies to other antigens.

Such is the case in serologic testing for HLA-B27, as the antisera reactive with this antigen also frequently cross-react with HLA-B7, —B22, —B40 and other antigens. Thus, at present, it is often recommended that a complete antigenic profile of all detectable HLA-A and —B antigens be performed to accurately determine expression of the HLA-B27 antigen.

Attempts have been made to replace this system with one based on monoclonal antibodies. It was believed that in view of the purity and restricted specificity of monoclonal antibodies, they would have potential for refining existing knowledge of the HLA system, as well as defining new HLA antigen relationships. Many of the monoclonal antibodies actually produced, however, recognized supertypic specificities shared by different alleles and occasionally by antigens of different loci. Thus, although several antibodies have been isolated which react with the B27 antigen, they also cross-react with numerous other B antigen alleles. Monoclonal antibodies with more restricted specificities have recently been reported, but show a concomitant loss of the ability to bind all of the known B27 variants.

Therefore, there exists a need for cell lines capable of producing a receptor, such as monoclonal antibody, specific for human HLA-B27 antigen, but which does not significantly cross-react with other HLA antigens, particularly other B locus alleles. Further, the receptor or monoclonal antibody should be capable of recognizing the polymorphic epitopic site of human HLA-B27 antigen across the various human races. The present invention fulfills this need.

Brief Description of the Relevant Literature

Several antibodies capable of reacting with HLA-B27 antigen and several other B locus alleles have been reported. See, Ellis et al., *Hum. Immunol.* (1982) 5:49; Rebai et al. (1983) 17:357; Trapani et al., *Hum. Immunol.* (1983) 7:205; Antonelli et al., AACHT abstract, 1983. Grumet et al., *Hum. Immunol.* (1982) 5:61, describe a monoclonal antibody (B27M2) which divides HLA-B27 into two subgroups, and also recognizes B47. The possible identification of subtypes of B27 with conventional sera or by cytotoxic T lymphocytes are provided in de Waal et al., *Histocompatibility Testing* 1984, eds. E. D. Albert et al., Springer-Verlag Press, Berlin, 1984, p. 418 and Breuning et al., *Hum. Immunol.* (1982) 5:259–268. Breur and Ivanyi, *Histocompatibility Testing* 1984, Eds. E. D. Albert et al., Springer-Verlag Press, Berlin, 1984, p. 144, describe qualities of four anti-B27 monospecific typing sera across four human races.

SUMMARY OF THE INVENTION

Methods and compositions are provided which permit the specific detection of human HLA-B27 antigen. Hybrid cell lines are produced that secrete monoclonal antibodies specific for the HLA-B27 antigen, but which do not cross-react with other HLA alloantigens. The hybrid cell lines can serve as a source of DNA for preparation of receptors specific for HLA-B27 by hybrid DNA technology or for fusing with other cells to transfer the chromosome carrying the genes for production of the antibodies of the present invention, thus providing other cellular means for producing HLA-B27 specific receptors. The monoclonal antibodies or receptors specific for HLA-B27 antigen are useful in diagnosis and therapy.

DESCRIPTION OF THE SPECIFIC EMBODIMENTS

In accordance with the present invention, novel cells and compositions are provided for the specific recognition of the human alloantigen HLA-B27. The subject cells have an identifiable chromosome, in which the germ-line DNA has rearranged to encode a receptor having a binding site specific for an epitopic site found on the alloantigen HLA-B27, but not found on other related or unrelated HLA alloantigens. These receptors, typically monoclonal antibodies, can be used in a wide variety of ways, including diagnosis and therapy.

The preparation of monoclonal antibodies can be accomplished by immortalizing nucleic acid sequences capable of expressing receptors specific for the human HLA-B27 private epitope, by introducing such sequences, typically cDNA encoding for the receptor, into a host capable of cultivation in culture. The immortalized cell line may be a mammalian cell line that has been transformed through oncogenesis, by transfection, mutation, or the like. Such cells include myeloma lines, lymphoma lines, or other cell lines capable of supporting the expression and secretion of the receptor in vitro. The receptor may be a naturally-occurring immunoglobulin of a mammal other than human, produced by transformation of a lymphocyte, particularly a splenocyte, by means of a virus or by fusion of the lymphocyte with a neoplastic cell, e.g., a myeloma, to produce a hybrid cell line. Typically, the splenocyte will be obtained from an animal immunized against the human B—27 antigen or a fragment thereof containing an epitopic site. Immunization protocols are well known and can vary considerably yet remain effective (See, Golding, *Monoclonal Antibodies: Principles and Practice*, Academic Press, N.Y. (1983), which is incorporated herein by reference).

Alternatively, the receptor may be an immunoglobulin produced by hybrid DNA techniques, where for example, genomic DNA or cDNA coding for one or both heavy and light chains of the anti-HLA-B27 monoclonal antibodies is inserted into an expression vector for expression of the chains. See generally, U.S. Nos. 4,172,124; 4,350,683; 4,363,799; 4,381,292; and 4,423,147. See also, Kennett et al., *Monoclonal Antibodies*, Plenum, N.Y., (1980), and references cited therein, all of which are incorporated herein by reference.

The hybrid cell lines may be cloned and screened in accordance with conventional techniques, and antibodies in the cell supernatants detected that are capable of binding to the polymorphic or private sites of human HLA-B27 determinants. The appropriate hybrid cell lines may then be expanded in vitro or injected into the peritoneal cavity of an appropriate host for production of ascites fluid. By virtue of having the antibody of the present invention, which is known to be specific for the B27 polymorphic site, the supernatants may be screened in competition with the subject monoclonal antibodies in a competitive assay. Thus, hybrid cell lines can be readily produced from a variety of sources based on the availability of present antibodies specific for the particular polymorphic site. Alternatively, where hybrid cell lines are available that produce antibodies specific for the subject polymorphic site, these hybrid cell lines may be fused with other neoplastic B-cells, where such other B-cells may serve as recipients for genomic DNA coding for the receptors.

While rodent, particularly murine, neoplastic B-cells are preferred, other mammalian species may be employed, such as lagomorpha, bovine, ovine, equine, porcine, avian or the like, which animals can provide lymphocytes, particularly splenocytes, for fusion and will recognize the human HLA-B27 polymorphic site as antigenic. The monoclonal antibodies may be of any of the classes or subclasses of immunoglobulins, such as IgM, IgD, IgA, $IgG_{1-4}$, or IgE. As IgG is the most common isotype utilized in diagnostic assays, it is preferred.

One specific embodiment of the present invention is the hybrid cell line designated GS145.2, which was generated by fusing NS-1 myeloma cells with spleen cells from a $CB6F_1$ mouse immunized with B27-positive human lymphoid cells. The fusion was performed as described in Nowinski, et al., *Virology* (1979) 93:111; and Hanson, et al., *Immunogenetics* (1980) 10:247. After primary screening and cloning by limiting dilution, the clone GS145.2 was employed to produce ascites fluid in BALB/c mice, which provided an immunoglobulin that was characterized as $IgG_1$ and that was specific for the polymorphic determinant of human HLA-B27.

In accordance with hybrid DNA technology, the receptors of the present invention may be produced in various hosts (See, Boss, et al., *Nucl. Acid. Res.*, 12:3791 and Wood et al., *Nature* 314:446, both of which are incorporated herein by reference. For example, the messenger RNA transcribed from the genes coding for the light and heavy chains of the monoclonal antibodies produced by the GS145.2 cell line may be isolated by differential cDNA hybridization employing cDNA from BALB/c lymphocytes other than the subject clone. The GS145.2 mRNA that does not hybridize will be rich for the messages coding for the desired immunoglobulin chains. As necessary, this process can be repeated to further enhance the the desired mRNA levels. The subtracted mRNA composition may then be reversed-transcribed to provide for a cDNA mixture enriched for the desired sequences. The RNA may be hydrolyzed with an appropriate RNase and the ssDNA made double-stranded with DNA polymerase I and random primers, e.g., randomly fragmented calf thymus DNA. The resulting dsDNA may then be cloned by insertion into an appropriate vector, e.g., virus vectors, such as lambda vectors or plasmid vectors (such as pBR322, pACYC184, etc.). By developing probes based on known sequences for the constant regions of the light and heavy chains, those cDNA clones having the gene coding for the desired light and heavy chains can be identified by hybridization. Thereafter, the genes may be excised from the plasmids, manipulated to remove superfluous DNA upstream from the initiation codon, and then introduced in an appropriate vector for transformation of a host and ultimate expression of the gene.

Conveniently, mammalian hosts may be employed which can properly process the chain so as to join the heavy and light chains to produce an intact immunoglobulin, and furthermore, secrete the immunoglobulin free of the leader sequence, if desired. Alternatively, one may use unicellular microorganisms for producing the two chains, where further manipulation may be required to remove the DNA sequences coding for the secretory leader and processing signals, while providing for an initiation codon at the 5' terminus of the sequence coding for the heavy chain. In this manner, the immunoglobulins can be prepared and processed so as to be assembled and glycosylated in cells other than murine cells. If desired, each of the chains may be truncated so as to retain at least the variable region, which regions may then be manipulated to provide for other receptors specific for the human HLA-B27 polymorphic determinant.

The monoclonal antibodies of the present invention are particularly useful because of their specificity for human HLA-B27 antigen across all B27 variants presently known. Other prior monoclonal antibodies fail to recognize B27 on the cells of some oriental donors and on the cells of approximately 20% of Caucasian donors. Also, the monoclonal antibody secreted by the GS145.2 cell line is of the IgG isotype, permitting easier incorporation into diagnostic assays, as well as other utilities.

Monoclonal antibodies of the present invention can find a wide variety of utilities, both in vivo and in vitro. By way of example, for in vitro uses, the monoclonal antibodies can be utilized for cell typing, for isolating B27 positive cells, for selectively killing B27 positive cells, for selectively killing B27 positive cells in a heterogeneous mixture of cells, or the like. For diagnostic purposes, the monoclonal antibodies may either be labeled or unlabeled. Typically, diagnostic assays entail the detection of a formation of a complex through the binding of the monoclonal antibody to the B27 antigen. When unlabeled, the antibodies find use in agglutination or complement-mediated cytotoxicity assays, or in combination with other, labeled antibodies (second antibodies) reactive with the monoclonal antibody, such as antibodies specific for immunoglobulin of the particular host species of the subject monoclonal antibody. A wide variety of labels may be employed, such as radionuclides, fluorescers, enzymes, enzymes substrates, enzyme cofactors, enzyme inhibitors, ligands (particularly haptens), etc. Numerous types of immunoassays are available, and by way of example, some include those described in U.S. Pat. Nos. 3,817,827; 3,850,752; 3,901,654; 3,935,074; 3,984,533; 3,996,345; 4,034,074; and 4,098,876, all of which are incorporated herein by reference.

The antibodies can be utilized in various commercial systems, such as flow microfluorometers, where the fluorescent conjugated antibodies may be used alone or in conjunction with other antibodies specific for HLA-antigens. Typically, the cells are counted and sorted as to their histocompatibility type. Fluorescers of interest include fluorescein, Texas red, rhodamine, umbelliferone, phycobiliproteins, dansyl, and the like.

Commonly, the monoclonal antibodies of the present invention are utilized in enzyme immunoassays, where the subject antibodies, or second antibodies from a different species, are conjugated to an enzyme. When a sample containing human cells, such as human blood or lysate thereof, is confined with the subject antibodies, binding occurs between the antibodies and those cells (or proteins) exhibiting the B27 antigen. Such cells may then be separated from the binding materials, and a second antibody (labeled with an enzyme) added. Thereafter, the presence of the antibody-enzyme conjugate specifically bound to the cells is determined. Other conventional techniques well known to those skilled in the art may also be utilized.

Kits can also be supplied for use with the subject antibodies in the detection of human HLA cell type or for the presence of the B27 antigen. Thus, the subject monoclonal antibody composition of the present invention may be provided, usually in a lyophilized form, either alone or in conjunction with additional antibodies specific for other HLA alloantigens. The antibodies, which may be conjugated to a label or unconjugated, are included in the kits with buffers, such as Tris, phosphate, carbonate, etc., stabilizers, biocides, inert proteins, e.g., bovine serum albumin, or the like. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody is employed capable of binding to the monoclonal antibody, this will usually be present in a separate vial. The second antibody is typically conjugated to a label and formulated in an analogous manner with the antibody formulations described above.

As indicated previously, the typing of an individual for HLA-B27 is very useful for diagnosing the likelihood of various rheumatic disorders. Those skilled in the art will realize that the monoclonal antibodies of the present invention will also find use in numerous additional ways, such as affinity chromotography, purification of the B27 antigen, separation of cells containing the B27 antigen from cells lacking such antigen (typically involving cytotoxic reactions), and the like. See generally, *Immunological Methods*, Vols. I and II, eds. Lefkovits, I. and Pernis, V., Academic Press, New York (1979 and 1981); and *Handbook of Experimental Immunology*, ed. Weir, D., Blackwell Scientific Publications, St. Louis, Mo. (1978), both of which are incorporated herein by reference.

Other features and advantages of the present invention will become apparent from the following experimental description, which describes the invention by way of example. The examples are offered by way of illustration and not by way of limitation.

EXPERIMENTAL

Production of Monoclonal Antibody GS145.2

CB6F$_1$ mice were immunized with HLA B27 antigen on B lymphoblastoid cells established from an ankylosing spondylitis patient. Mice were immunized by two subcutaneous injections without adjuvant given 32 days apart. Spleens were removed three days following the last injection.

Splenic B lymphocytes from the immunized mice were fused with NS1-1 myeloma cells using 40% (w/v) polyethylene glycol (Kohler and Milstein, Nature 256:495 (1975)). Following fusion the cell mixture was resuspended in HAT medium (RPMI-1640 medium supplemented with 20% bovine serum, $1 \times 10^{-4}$M hypoxanthine, $4 \times 10^{-7}$M aminopterin and $1.6 \times 10^{-5}$M thymidine) to select for growth of hybrid cells, and then dispensed into a 96-well microculture tray at a concentration of 1 to $3 \times 10^6$cells/ml.

Cells producing antibody to B27 were identified by an enzyme-linked microimmunoassay measuring binding to human leukocytes (see below). The hybrid cell line was established by three cycles of cloning by limiting dilution using syngeneic thymocytes as feeder cells. The line was deposited with the A.T.C.C. on Jun. 28, 1985, and given Accession No. HB8856.

Monoclonal antibody protein was isolated by conventional means from ascites fluid using ion exchange chromatography. Ascites fluid was obtained by growth of hybridoma cells in the peritoneal cavity of syngeneic mice primed one to four weeks earlier with an intraperitoneal injection of pristane. The isotype of the monoclonal antibody was determined by ELISA in accordance with standard procedures.

Cell Panel

Specificity of GS145.2 was determined by assaying reactivity to a panel of T lymphocytes from 40 normal individuals and a panel of B lymphoblastoid lines from 10 ankylosing spondylitis patients and 15 normal donors. The HLA type of each donor was determined by an independent reference HLA laboratory using conventional microcytotoxicity assay. T lymphocytes were obtained from peripheral blood by density gradient centrifugation on Ficoll-Hypaque and passage through nylon wool (Danilovs et al., 8th *International Histocompatibility Workshop Newsletter* (1978) 6: 3). B lymphoblastoid lines were obtained from peripheral B lymphocytes transformed with Epstein-Barr virus.

Micro-Enzyme-Linked Immunosorbent Assay (ELISA) to Detect Monoclonal Antibody Binding to HLA Antigens This assay was used in an indirect mode to identify hybridomas secreting antibody to HLA-B27 antigens. Terasaki microtrays were prepared by addition to each well of 5 μl of a 1 μg/ml solution of poly-L-lysine in phosphate buffered saline (PBS). The plates were incubated at 37° C. for 1 hr and washed with PBS by immersion and decanting. Human leukocytes were dispensed into each well: 1 μl of a suspension of 1 to $5 \times 10^6$ cells per ml of RPMI-1640 medium without serum. The plates were centrifuged at 90 g for 3 min. A solution of 1% bovine serum albumin (BSA) in PBS with 0.2% azide was added to the plates, which were then stored at 4° C. for 1 to 48 hr. Before adding antibody, the plates were washed three times.

Monoclonal antibody was added, 1 μl per well. After 1 hr at room temperature, the plates were washed five times and a solution of the F(ab')$_2$ fragment of anti-immunoglobulin coupled with horseradish peroxidase (HRP) was added, 5 μl per well. The plates were then incubated at room temperature for 30 to 60 min.

After treatment with antibody the trays were washed five times. The presence of HRP-antibody complexes in the wells was visualized by the addition of a solution of substrate, hydrogen peroxide, and chromagen, ABTS® (Boehringer-Mannheim Biochemicals, Indianapolis, Ind.) in 0.1M sodium citrate pH4.2. Development of color in wells after 30 to 60 min incubation at room temperature indicated binding of monoclonal antibody to leukocytes in those wells.

Analysis of the Specificity of Monoclonal Antibodies by Immunoprecipitation of Labeled HLA Antigens Membrane proteins of lymphoblastoid cells were labeled with $^{125}$I using lactoperoxidase (Vitetta et al., *J. Exp. Med.* (1971) 134:242). Cells were disrupted in buffer containing 0.5% Nonidet P-40 (Sigma Chemical Company) and cleared by centrifugation, both before and after addition of control antibody and solid phase immunoadsorbent. Monoclonal antibodies were added to aliquots of the lysate and complexes of antibody and labeled antigen precipitated using rabbit antibody to mouse immunoglobulin coupled to a solid phase. After extensive washing, the labeled antigens were released by addition of sample electrophoresis buffer either as required for the Laemmli method of electrophoresis in polyacrylamide gels (*Nature* 227:680–685 (1970)) or as specified for the isoelectric focusing gel electrophoresis method of Yang et al., *Immunogenetics*, 19:217–231 (1984). Electrophoresis was conducted as required for each method. Labeled proteins in the dried gels were identified by autoradiography.

Analysis of the Specificity of Monoclonal Antibodies Labeled with Fluorescein Isothiocyanate (FITC) Using a Fluorescence-Activated Cell Sorter (FACS)

Monoclonal antibody isolated from ascites was conjugated to FITC according to the method of Goding (Goding, *J. Immunol. Methods* (1976) 13:215). Cells to be analyzed were mixed with saturating amounts of FITC-conjugated antibody and incubated for 30 min at 4° C. Treated cells were washed and the amount of bound antibody assessed by comparing the fluorescence intensity (mean modal) of cells incubated with test and control antibodies on a FACS IV (Becton-Dickinson) fitted with a log amplifier.

Results

A series of immunizations and fusions was performed as described above to generate monoclonal antibody to HLA-B27. GS145.2 was selected from one well of approximately 8000 screened. The antibody produced by GS145.2 was determined to be of the IgG$_1$ isotype.

The specificity of GS145.2 was determined using the microelisa assay. It has been tested on 25 B-lymphoblastoid cell lines from ankylosing spondylitis patients or normal individuals, and on T cells from 40 normal individuals selected for expression of B27 or of alleles known to cross-react with B27. GS145.2 reacted with all cells expressing B27. Results of microelisa assays on 25 T cells are given in Table I.

TABLE I

T lymphocytes from 25 donors tested for expression of HLA-B27 using GS145.2 in microelisa assay

| Donor HLA Type* | | Reaction |
|---|---|---|
| A3,26 | B27,35 | + |
| 3,25 | 27,35 | + |
| 2,11 | 27,38 | + |
| 11,31 | 27,35 | + |
| 2,28 | 27,60 | + |
| 2,24 | 27,44 | + |
| 1,26 | 27,57 | + |
| A3,31 | B35,39 | − |
| 11,52 | 51,59 | − |
| 2,3 | 50,60 | − |
| 2,23 | 45,55 | − |
| 1,2 | 51,57 | − |
| 1 | 7,8 | − |
| 1 | 8,44 | − |
| 1,30 | 18,57 | − |
| 2 | 35,36 | − |
| 2,32 | 44,X | − |
| 2,24 | 13,44' | − |
| 2 | 7,14' | − |
| 1,28 | 8,47 | − |
| 3,29 | 8,47 | − |
| 1,26 | 38,57 | − |
| 2,32 | 35,57 | − |
| 26,32 | 58,60 | − |
| 1,2 | 51,58 | − |

*HLA types of donors determined by microcytotoxicity testing at an independent reference laboratory.

GS145.2 reacted with T cells from 7 of the 7 people expressing HLA-B27. No other cells tested as positive. The negative cells included those expressing B7 (3), B47 (1), B60 (3), B17 (6), B22 (2) or A32 (4). These HLA-B alleles do test as positive with some alloantisera or other monoclonal antibodies to B27.

The specificity of GS145.2 was also tested in an indirect immunoflourescence assay. The cells used were a B-lymphoblastoid cell line expressing B27 on one haplotype (T51), a mutant line derived from the first which expresses low levels of B27 (4.59.8), and an unrelated line not expressing B27 (MRO). Binding of GS145.2 or control antibodies was detected using fluoresceinated antibody to mouse immunoglobulin and analysed on a FACS IV cell sorter fitted with a log amplifier (Becton-Dickinson, Mountain View, Calif.). The results are presented in Table II. The positive cells were distributed in a single asymmetrical peak. When reacted with GS145.2, the B27 positive cells were 100 channels brighter than the mutant cells which expressed low levels of B27.

TABLE II

FACS analysis of the specificity of GS145.2

| Cell | HLA-B | Peak channel of fluorescence | | |
|---|---|---|---|---|
| | | GS145.2 | Negative Control | Positive Control |
| T51 | 8,27 | 206 | 48 | 225 |
| 4.59.8 | 8,- | 104 | 56 | 203 |
| MRO | 8,44 | 95 | 46 | 153 |

Confirmation that GS145.2 bound to B27 was provided by radioimmunoprecipitation followed by isoelectric focusing in polyacrylamide gels and autoradiography to visualize labeled proteins. B cell lines used as the source of HLA antigens were AS4 (B27,38) and AS6 (B27,40). Only bands corresponding to B27 were present in the GS145.2 precipitates.

From the foregoing, it will be appreciated that the cell lines of the present invention provide monoclonal antibodies and other receptors specific for human HLA-B27 antigen, but which do not substantially cross-react with other HLA antigens. This allows sensitive assays to be developed which can detect this antigen on cells in the presence of other closely related antigens (e.g., alleles). In addition, the cell lines provide a means to readily and economically produce large quantities of the receptors, which find uses in immunoassays, immunohistochemical stainings, immunoabsorbent and cell sorting procedures.

Although the present invention has been described in some detail by way of illustration and example for purposes of clarity of understanding, it will be obvious that certain changes and modifications may be practiced within the scope of the appended claims.

What is claimed is:

1. A monoclonal antibody composition specific for the human HLA-B27 antigen, not cross-reactive with HLA-B22, and not substantially cross-reactive with HLA-B7, —B14, and —B47 antigens.

2. A monoclonal antibody composition according to claim 1, wherein said monoclonal antibody is murine.

3. A monoclonal antibody composition according to claim 2, wherein said monoclonal antibody is obtained from a cell line designated ATCC Accession No. HB 8856.

4. A monoclonal antibody composition according to claim 1 and which competes for binding to the B27 antigen in a competition assay with a monoclonal antibody composition obtained from a cell line designated ATCC Accession No. HB 8856.

5. A monoclonal antibody composition according to claim 1, wherein said antibody is of the class IgG.

6. A monoclonal antibody composition according to claim 1, bound to a second antibody specific for said monoclonal antibody composition and conjugated to a label capable of providing a detectable signal.

7. A monoclonal antibody composition according to claim 1, conjugated to a label capable of providing a detectable signal.

8. A monoclonal antibody composition according to claim 7, wherein said label is a fluorescer.

9. A monoclonal antibody composition according to claim 7, wherein said label is an enzyme.

10. A method for detecting the presence of human cells having the HLA-B27 antigen, which comprises combining the human cells with a monoclonal antibody composition specific for the human HLA-B27 antigen, not cross-reactive with HLA-B22, and not substantially cross-reactive with HLA-B7, —B14, and —B47 antigens and detecting complex formation and relating the presence of complex formation with the presence of cells having the B27 antigen.

11. The method of claim 10 wherein complex formation is detected by complement-mediated lysis.

12. A method for detecting the presence of human cells having the HLA-B27 antigen according to claim 10, wherein said monoclonal antibody is murine.

13. A method for detecting the presence of human cells having the HLA-B27 antigen according to claim 10, wherein said monoclonal antibody is obtained from a cell line designated ATCC Accession No. HB8856.

14. Method for detecting the presence of human cells having HLA-B27 antigen according to claim 10, wherein the monoclonal antibody composition is cross-reactive with a monoclonal antibody composition obtained from a cell line having ATCC Accession No. HB8856.

15. A method for detecting the presence of human cells having HLA-B27 antigen according to claim 10, wherein the monoclonal antibody composition is conjugated to a label capable of providing a detectable signal.

16. A method for detecting the presence of human cells having HLA-B27 antigen according to claim 15, wherein said label is a fluorescer.

17. A kit for use in detecting the presence of human cells having the HLA-B27 antigen, said kit comprising a container having a monoclonal antibody composition specific for the polymorphic epitopic site of human HLA-B27 antigen, not cross-reactive with HLA-B22 and not substantially cross-reactive with HLA-B7, —B14, and —B47 antigens, wherein either the monoclonal antibody composition or a second antibody contained in a separate container reactive with the monoclonal antibody composition is conjugated to a label, providing a detectable signal.

18. The hybrid cell line designated ATCC accession number HB-8856.

* * * * *